United States Patent [19]

Flynn

[11] Patent Number: 4,970,907

[45] Date of Patent: Nov. 20, 1990

[54] TRANSDUCER HOLDER

[75] Inventor: John J. Flynn, Los Angeles, Calif.

[73] Assignee: The California Province of the Society of Jesus, Los Gatos, Calif.

[21] Appl. No.: 253,276

[22] Filed: Oct. 4, 1988

[51] Int. Cl.⁵ .............................................. G01D 11/30
[52] U.S. Cl. ..................................... 73/866.5; 73/1 R
[58] Field of Search ...................... 73/866.5, 431, 618, 73/1 R, 596, 644, 855; 310/348, 354, 336

[56] References Cited

U.S. PATENT DOCUMENTS

| | | | |
|---|---|---|---|
| 4,158,309 | 6/1979 | Elsner et al. | 73/641 |
| 4,170,145 | 10/1979 | Kennedy et al. | 73/618 |
| 4,327,591 | 5/1982 | Dybel et al. | 73/855 |

Primary Examiner—Jerry W. Myracle
Attorney, Agent, or Firm—Lyon & Lyon

[57] ABSTRACT

A transducer holder that is mountable to a test object includes a pair of clamping members and clamp closing members to instantaneously tighten the clamping members on the transducer and hold it in optimum position for obtaining elevational resolution (out-of-plane beam width) measurements with a slice thickness test object.

12 Claims, 2 Drawing Sheets

TRANSDUCER HOLDER

BACKGROUND OF THE INVENTION

The field of the present invention is ultrasonic medical diagnostic equipment for non-destructive testing and non-invasive examination of soft-tissue and body organs and specifically equipment for testing the accuracy of and calibrating ultrasonic diagnostic equipment such as pulse echo body scanners and the like.

Apparatus and techniques which permit the non-destructive testing and non-invasive examination of soft tissue and body organs are of particular interest to the medical community. Examples of presently available techniques include x-ray, nuclear medicine, thermography and diagnostic ultrasound. Ultrasonic diagnostic techniques are important because they offer a very high benefit to risk ratio for the patient and the ability to perform quality imaging of soft tissue organs. Ultrasonic diagnosis has found widespread applicability to the medical subfields of obstetrics, gynecology, cardiology, neurology, opthalmology, and urology, among others. Ultrasonic diagnostic has proved of particular value as a diagnostic aid for the pregnant uterus including fetus and placenta, eye, breast, brain, lung, kidney, liver, gall bladder, bile ducts, pancreas, spleen, heart and blood vessels and soft tissues of the neck, including thyroid and parathyroid glands.

Ultrasonic diagnostic instruments operate on either a pulse-echo or Doppler principle. These principles are both well known. Most frequently the imaging of soft body tissue is accomplished using the pulse-echo principle. Short bursts of ultrasonic energy are transmitted into the body and the echoes are recorded. The time required for an emitted pulse to return as an echo provides an indication of the distance of a measured structure. Echoes occur at the boundaries between different tissues within the body since a fraction of the incident energy is deflected whenever the characteristic impedance of the structure under examination changes. Typically a change in the characteristic impedance occurs at such a boundary. Impedance is defined as the product of the density of the tissue multiplied by the velocity of sound. The first boundary will not typically reflect all the energy which may be reflected at subsequent boundaries. Thus, various boundaries at various depths can be observed.

Ultrasonic diagnostic equipment is used by a process called scanning. Scanning involves the movement of a pulsed sound beam promulgated by a transducer through a scanning plane. The transducer converts electrical signals into acoustic pulses and converts the returning echoes back into electrical signals. Through scanning, a two dimensional image of the various organs or body regions of interest can be generated.

The quality of the two-dimensional image generated through the scanning process is dependent on the axial, lateral and elevational (i.e., out-of-plane) resolution of the transmitted ultrasonic beam and the absence or presence of side lobes. Resolution is also substantially dependent on the cross-section of the ultrasonic beam of various depths. Various methods and devices have been proposed for determining axial and lateral resolution of the ultrasonic beam and the beam within the direction of the scanning plane. In a copending application, Ser. No. 097,599 now U.S. Pat. No. 4,903,523, an apparatus and method are disclosed for measuring the out-of-plane width (i.e., elevational resolution) of the beam. This measurement is important because ultrasonic testing equipment operates on the fictitious assumption of a strictly one dimensional beam. Because the beam is actually three dimensional, out-of-plane reflections from objects in the scanning volume may be displayed as if they were within the theoretical scanning plane, thus creating undesirable image effects. Copending application Ser. No. 097,599 discloses a test object comprising one or more wedge-shaped clusters of targets whose apices are positioned in the scanning plane. By placing a series of target clusters at different depths, out-of-plane beam width (elevational resolution) can be measured throughout the scanning range.

In order to assure accuracy in imaging out-of-plane beam width, it is necessary to orient the transducer such that the scanning plane passes through the apex or apices of the target wedge(s). If the transducer is allowed to pivot or rotate such that the scanning plane does not pass through the target apex or apices, inaccurate measurements may result. In the present state of the art, the ultrasonic transducer is hand held for positioning the transducer on the scanning surface of the test object or within an open tank of water containing the test object. This procedure requires considerable skill and patience to obtain and maintain control of the optimum position of the transducer in relation to the test object which is essential for accurate measurement of the beam slice thickness. Because the optimum position of the transducer requires that the scan plane coincide with the plane of the wedge apices, misalignment over two degrees of freedom of motion along the vertical and longitudinal axis of the transducer must be avoided. Thus, means for fixing a transducer with respect to a desired scanning plane would be advantageous.

SUMMARY OF THE INVENTION

The present invention is directed to a device for immobilizing an ultrasonic transducer during operation thereof at a predetermined position and orientation. To that end, clamping means are provided to position and fix the transducer as desired.

DETAILED DESCRIPTION OF THE PREFERRED EMBODIMENT

Figure 1:
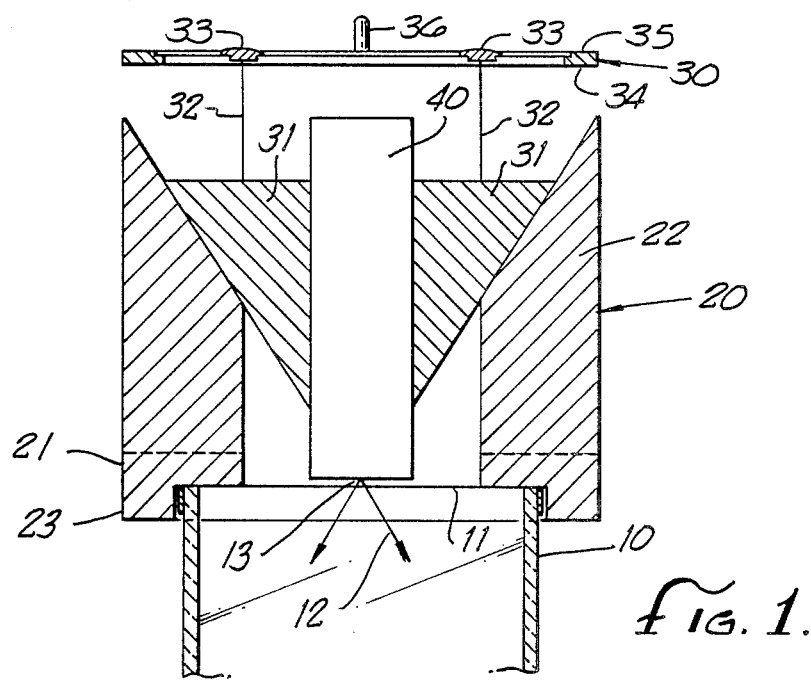
FIG. 1 is an end view of a transducer holder constructed in accordance with one embodiment of the present invention.

Referring to FIG. 1, the upper portion of a test object 10 is shown suitable for determining slice thickness (elevational resolution) of an ultrasound beam (not shown) as it passes through the scanning window 11 of the test object 10 to strike the sides of the wedge-shaped scan target 12 centered at its apex 13.

The base section 20 of the transducer holder comprises a frame 21 to which are fixed two bilaterally symmetrical stanchions 22 with sloping upper surfaces. The frame 21 has a lip 23 which overhangs the top of the test object 10 to which it is stabilized horizontally by reason of the lip 23 extending around the perimeter of the test object 10. Thus, the lip 23 of the transducer holder prevents the base section 20 from being displaced laterally or longitudinally with respect to the test object. The stanchions 22 provide positioning means by which the position of the transducer may be precisely fixed. The sloping upper surfaces of the stanchions extend downwardly and medially toward the test object.

The upper section 30 of the transducer guide comprises two bilaterally symmetrical prism-shaped jaws or clamping members 31 that are suspended from two rigid support rods 32, each of which are attached to encasements 33 containing ball-bearings (not shown) which roll freely along tracks 34 extending in the clamping member support plate 35 of the upper section 30. A handle 36 is attached to the clamping member support plate 35.

The clamping members 31 serve to lock the transducer at a fixed location. The clamping members 31 have parallel vertical inner surfaces adapted to grip the sides of the transducer, and outer angled walls adapted to rest on the sloping upper surfaces of the stanchions 22. In combination, the clamping members 31 and the stanchions 22 form an adjustable clamp wherein the stanchions 22 serve as guide members adapted to position and support the clamping members 31 and as clamp closing members to impart a closing force thereon by weight of gravity of the upper section 30 and downward force applied by the operator to the handle 36.

Figure 2:
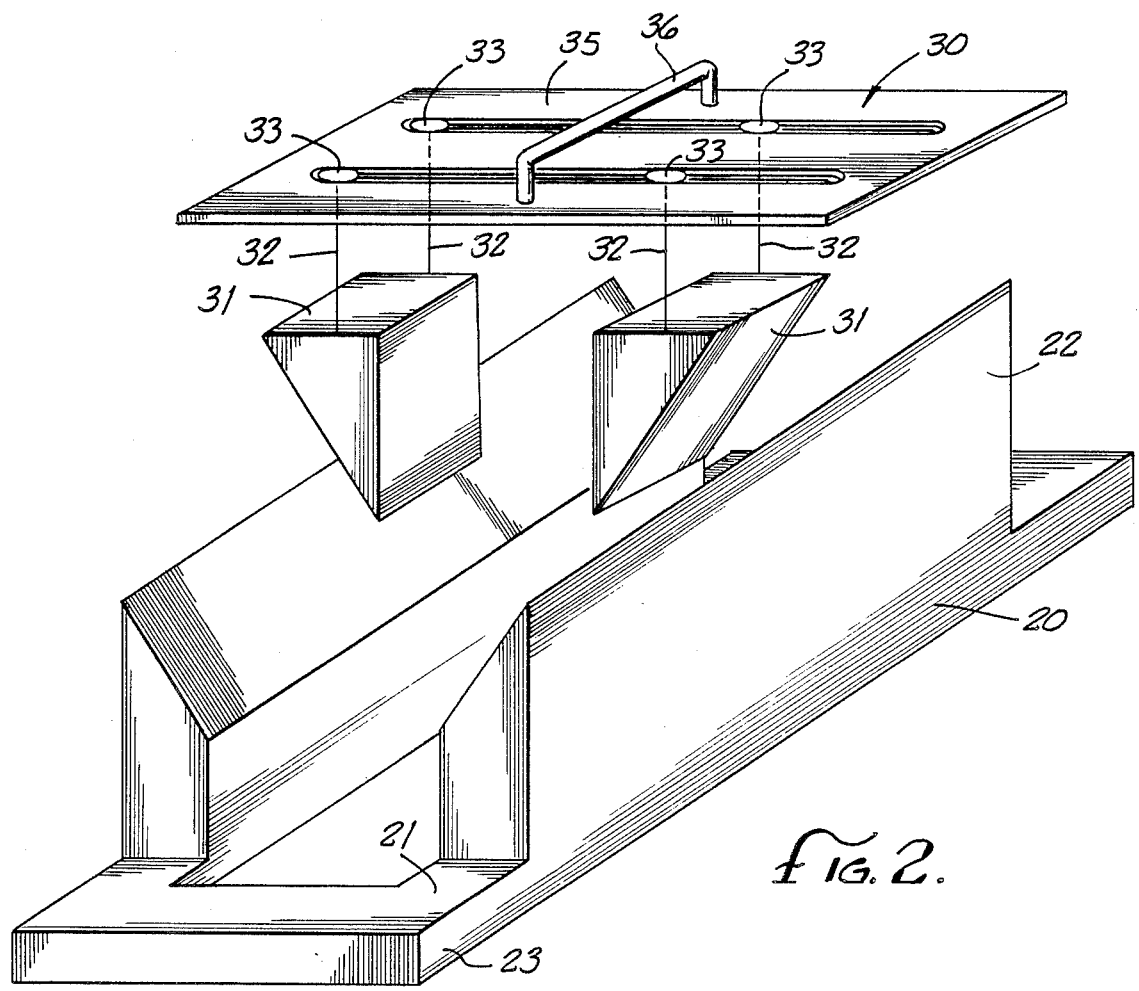
FIG. 2 is a perspective view of the upper section of the transducer holder of FIG. 1.

Referring to FIG. 2, the clamping members 31 are supported by rigid support rods 32 that are suspended from encasements 33 containing ball-bearings (not shown) which roll freely along tracks extending in the clamping member support plate 35 of the upper section 30. Other sliding arrangements would also be possible so long as the clamping members 31 are allowed to freely close and open when not engaged with the stanchions 22.

Figure 3:
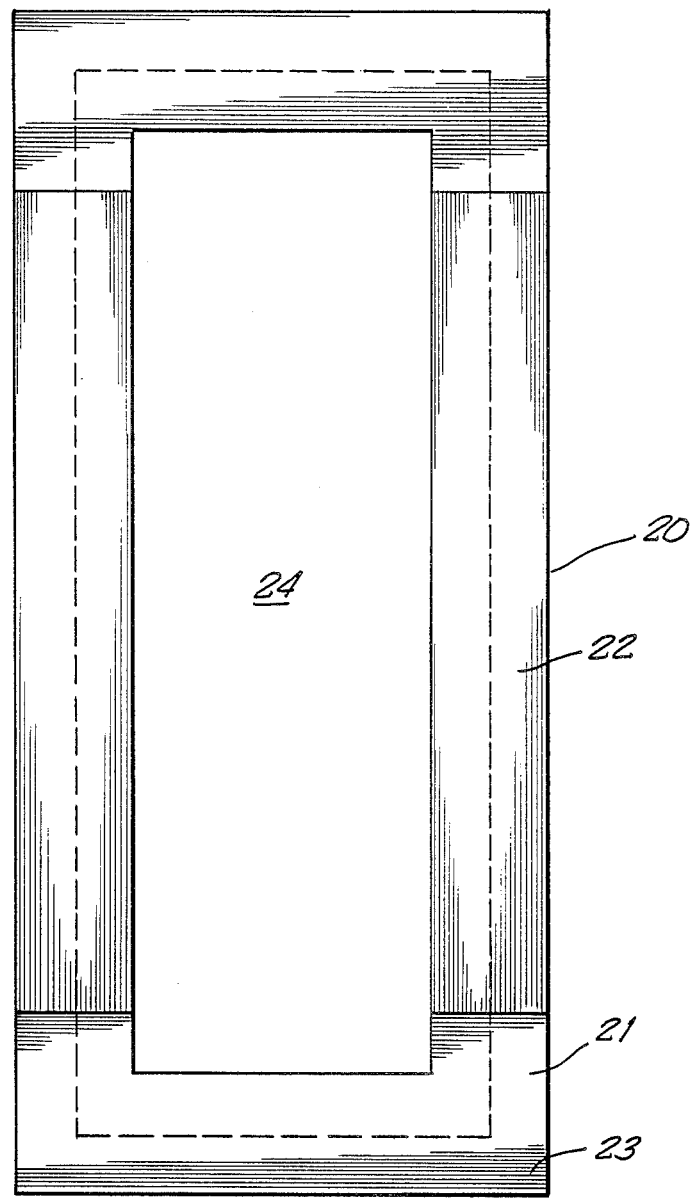
FIG. 3 is a plan view of a base section of the transducer holder of FIG. 1.
Figure 4:
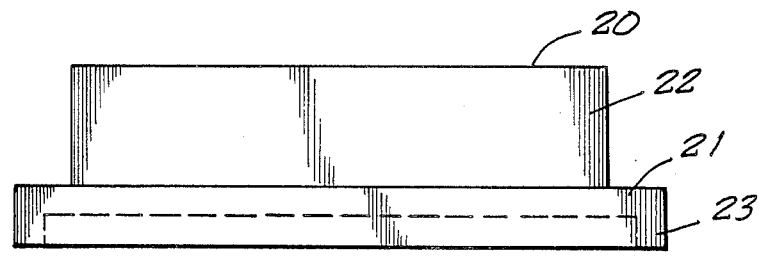
FIG. 4 is a side view of a base section of the transducer holder of FIG. 1.

Referring to FIG. 3, the frame 21 contains a central aperture 24 large enough to accept most standard size transducers. Referring to FIGS. 3 and 4, it is seen that the stanchions 22 need not extend the full length of the frame 21 so long as the transducer is suitably fixed for all testing positions.

The degree of slope of the bottom sides of the clamping members 31 are the right-angle compliment of the degree of slope of the upper surfaces of the stanchions 22. When the upper section 30 is lowered by the handle 36, the clamping members 31 are forced together so that their vertical inner sides clamp firmly to the outer sides of the transducer 40. The weight of gravity and moderate downward pressure by the operator on the handle are sufficient to secure the transducer firmly in an optimum position.

The transducer guide thus centers the transducer 40 to the test object and prevents its rotation from optimal positions in two degrees of freedom of motion with respect to its vertical and longitudinal axes. The third degree of freedom of motion of the transducer with respect to its transverse axis is controlled when using enclosed test objects by placing the flat surface of the transducer firmly on the flat horizontal membrane surface of the scanning window 11 of the test object 20.

While many material choices are available, it is contemplated that the frame 21, the stanchions 22, the clamping members 31 and the clamping member support plate 30 would be made of Lucite or other suitable material, and that the rigid support rods 32, the tracks 33 and the handle 36 would be formed of any suitable metal.

Thus, a transducer holder has been disclosed. While embodiments and applications of this invention have been shown and described, it would be apparent to those skilled in the art that many more modifications are possible without departing from the inventive concepts herein. The invention, therefore is not to be restricted except in the spirit of appended claims.

What is claimed is:

1. A transducer holder for positioning and retaining a transducer, comprising a base, a pair of transducer positioning stanchions mounted to said base, a pair of clamping members adapted for closure against a transducer by engagement with said positioning stanchions and a clamping member support plate, said clamping members being slidably attached to said support plate.

2. The holder set forth in claim 1 further including a handle mounted to said clamping member support plate.

3. The holder set forth in claim 1 wherein said clamping members are attached to said clamping member support plate by support rods mounted at one end to said clamping members and at the other end to encasements slidably arranged in tracks extending in said clamping member support plate.

4. The holder set forth in claim 3 wherein said support rods are slidably mounted to said clamping member support plate by encasements containing ball bearings mounted to roll freely along said tracks in said clamping member support plate.

5. A transducer holder for testing ultrasound diagnostic equipment in a test object comprising a frame having a lip extending around the top of said test object to securely position said frame with respect to said test object, a pair of stanchions extending along opposing sides of said test object substantially parallel to a scanning plane extending through said test object, said stanchions having sloping upper surfaces extending downwardly and medially toward said test object to provide positioning and support surfaces, a pair of clamping members having substantially vertical parallel inner surfaces adapted for closure against a transducer, and sloping outer surfaces adapted for engagement with the sloping upper surfaces of said stanchions such that said stanchions force said clamping members to a closed position against the sides of the transducer as said clamping members are urged toward the test object, a clamping member support plate having a handle attached thereto, said support plate having a pair of tracks formed therein, and rods mounted at one end to said clamping members and at the opposing end to encasements containing ball bearings mounted to roll freely along said tracks in said clamping member support plate, whereby movement of said handle toward the test object thrusts said clamping members against the sloping upper surfaces of said stanchions to impart a closing force on said clamping members to grip the transducer and whereby movement of the handle away from the test object releases the grip of said clamping members on the transducer.

6. A device for positioning and orienting an ultrasound transducer with respect to a test object comprising an adjustable clamp adapted for placement on the test object having a pair of clamping members, and self locking and unlocking means for closing said clamping members against the transducer at a predetermined position and orientation with respect to the test object.

7. The device set forth in claim 6 wherein said clamp closing means comprise a pair of guide members adapted to support said clamping members and impart a closing force thereon in response to movement of said clamping members toward the test object.

8. The device set forth in claim 7 further including handle means for moving said clamping members away from the test object and out of clamping engagement with the transducer.

9. A device for positioning and orienting an ultrasound transducer with respect to a test object comprising a clamp positionable on the test object and adapted to support the transducer at a predetermined position and orientation with respect to the test object, and a clamp closure structure configured to engage said clamp, said clamp closure structure imposing a clamp closure force on said clamp in response to movement of said clamp toward said test object.

10. A device for positioning and orienting an ultrasound transducer with respect to a test object comprising an adjustable clamp adapted for placement on the test object having a pair of clamping members and means for closing said clamping members against the transducer at a predetermined position and orientation with respect to the test object, said clamp closing means comprising a pair of guide members adapted to engage said clamping members and impart a closing force thereon in response to movement of said clamping members toward the test object.

11. A device for positioning and orienting said ultrasound transducer with respect to a test object comprising an adjustable clamp adapted for placement on a test object having a pair of clamping members and means for closing said clamping members against the transducer at a predetermined position and orientation with respect to the test object, said device further including handle means for moving said clamping members away from the test object and out of clamping engagement with the transducer.

12. A device for positioning and orienting an ultrasound transducer with respect to a test object comprising an adjustable clamp adapted for placement on the test object having a pair of clamping members, and means for closing said clamping members against the transducer, said clamp closing means exerting a closing force in proportion to the position of said clamping members with respect to the test object.

* * * * *